(12) United States Patent
Hwang et al.

(10) Patent No.: US 9,662,091 B2
(45) Date of Patent: May 30, 2017

(54) ULTRASONIC DIAGNOSTIC APPARATUS

(71) Applicant: SAMSUNG MEDISON CO., LTD., Gangwon-do (KR)

(72) Inventors: Won Soon Hwang, Hanam-si (KR); Gil Ju Jin, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 247 days.

(21) Appl. No.: 14/459,031

(22) Filed: Aug. 13, 2014

(65) Prior Publication Data

US 2015/0051494 A1    Feb. 19, 2015

(30) Foreign Application Priority Data

Aug. 13, 2013 (KR) .................. 10-2013-0095793

(51) Int. Cl.
*A61B 8/00*    (2006.01)
*G10K 11/00*    (2006.01)

(52) U.S. Cl.
CPC .......... *A61B 8/4461* (2013.01); *G10K 11/004* (2013.01)

(58) Field of Classification Search
CPC ......................... A61B 8/4461; G10K 11/004
USPC ............................................... 600/437–469
See application file for complete search history.

(56) References Cited

U.S. PATENT DOCUMENTS

| 4,375,818 A | * | 3/1983 | Suwaki | A61B 1/00177 600/101 |
| 5,555,887 A | * | 9/1996 | Fraser | A61B 1/0052 600/472 |
| 2004/0082858 A1 | * | 4/2004 | Fukuda | A61B 8/12 600/443 |
| 2009/0143682 A1 | | 6/2009 | Kadokura | |

(Continued)

FOREIGN PATENT DOCUMENTS

| DE | 835 239 | 3/1952 |
| EP | 1 576 926 A1 | 9/2005 |
| EP | 2 298 175 A1 | 3/2011 |

OTHER PUBLICATIONS

Extended European Search Report issued in counterpart European Patent Application No. 14173464.0 on Jan. 7, 2015; 8 pages.

(Continued)

*Primary Examiner* — Sanjay Cattungal
(74) *Attorney, Agent, or Firm* — McDermott Will & Emery LLP

(57) ABSTRACT

Disclosed herein is an ultrasonic diagnostic apparatus which includes a probe including a transducer installed to be rotatable, a driving device configured to rotate the transducer, at least one wire configured to transmit power of the driving device to the transducer, a handle case configured to accommodate the driving device therein, a cap coupled to the handle case to accommodate the transducer therein, and filled with oil, and a diaphragm formed of a deformable material and disposed between the cap and the handle case, wherein the wire is installed to pass through the diaphragm, (Continued)

and fixed to the diaphragm so that the diaphragm is deformed according to movement of the wire. Since the wire is fixedly installed to pass through the diaphragm and deformed according movement of the wire, oil in the cap is prevented from leaking to the handle case.

13 Claims, 15 Drawing Sheets

(56) References Cited

U.S. PATENT DOCUMENTS

| | | | |
|---|---|---|---|
| 2012/0010512 A1* | 1/2012 | O'Laughlin | A61B 8/12 600/461 |
| 2012/0157841 A1* | 6/2012 | Glaenzer | A61B 8/12 600/439 |
| 2013/0207517 A1* | 8/2013 | Naka | H01L 41/0533 310/334 |

OTHER PUBLICATIONS

European Office Action issued in European Patent Application No. 14173464.0, dated Nov. 30, 2015.

Communication pursuant to Article 94(3) EPC, issued in corresponding European Patent Application No. 14 173 464.0, mailed on Aug. 17, 2016.

* cited by examiner

ULTRASONIC DIAGNOSTIC APPARATUS

CROSS-REFERENCE TO RELATED APPLICATION

This application claims the benefit of Korean Patent Application No. P2013-0095793, filed on Aug. 13, 2013 in the Korean Intellectual Property Office, the disclosure of which is incorporated herein by reference.

BACKGROUND

1. Field

Embodiments of the present invention relate to an ultrasonic diagnostic apparatus having a probe which transmits ultrasonic waves to an object to be diagnosed and receives the ultrasonic waves reflected from the object.

2. Description of the Related Art

In general, ultrasonic diagnostic apparatuses radiate ultrasonic waves from a body surface of an object to be diagnosed to a region to be diagnosed in the body and obtain a tomography image of soft tissue or a blood flow image through the ultrasonic waves reflected from the region.

The ultrasonic diagnostic apparatuses include a body, a probe configured to transmit ultrasonic waves to an object and receive the ultrasonic waves reflected from the object, a display unit disposed at an upper portion of the body to display a diagnostic result obtained through the received ultrasonic waves using an image, and a control panel disposed in the front of the display unit to allow a user to operate the ultrasonic diagnostic apparatus.

Among the above-mentioned construction elements, the probe includes a transducer configured to transmit and receive the ultrasonic waves. Recently, there are ultrasonic diagnostic apparatuses in which the transducer is rotated to obtain a three-dimensional image.

SUMMARY

Therefore, it is an aspect of the present invention to provide an ultrasonic diagnostic apparatus which may easily rotate a transducer of a probe.

Additional aspects of the invention will be set forth in part in the description which follows and, in part, will be obvious from the description, or may be learned by practice of the invention.

In accordance with one aspect of the present invention, an ultrasonic diagnostic apparatus includes a probe including a transducer installed to be rotatable, a driving device configured to rotate the transducer, at least one wire configured to transmit power of the driving device to the transducer, a handle case configured to accommodate the driving device therein, a cap coupled to the handle case to accommodate the transducer therein, and filled with oil, and a diaphragm formed of a deformable material and disposed between the cap and the handle case, wherein the wire is installed to pass through the diaphragm, and fixed to the diaphragm so that the diaphragm is deformed according to movement of the wire.

The diaphragm may be formed of a stretchable material which is elastically deformed.

The probe may further include a partition member disposed between the cap and the handle case to partition an internal space of the cap and an internal space of the handle case, and the partition member may include a through-hole in which the diaphragm is installed.

The probe may further include a shaft connected to a rotational center of the transducer, and the wire may include a first wire connected to one side of the shaft so that the shaft is rotated in a first direction, and a second wire connected to the other side of the shaft so that the shaft is rotated in a second direction.

The diaphragm may include a first deforming portion through which the first wire passes to be fixedly installed therein and which is deformed according to movement of the first wire, and a second deforming portion through which the second wire passes to be fixedly installed therein and which is deformed according to movement of the second wire.

The probe may further include a first sealing member through which the first wire passes to be fixedly installed therein, installed to pass through the first deforming portion, and configured to seal between the first deforming portion and the first wire, and a second sealing member through which the second wire passes to be fixedly installed therein, installed to pass through the second deforming portion, and configured to seal between the second deforming portion and the second wire.

Each of the first deforming portion and the second deforming portion may have a bellows shape.

The driving device may include a driving motor configured to generate a rotational force, a transfer screw configured to be rotated by the driving motor, and a moving member configured to be moved in an axial direction of the transfer screw according to rotation of the transfer screw, and the first wire and the second wire may be connected to the moving member so that the first wire and the second wire are moved according to movement of the moving member.

The driving device may include a changing pulley configured to change an extending direction of the second wire, the first wire may have one end which is connected to one side of the moving member, and the other end which is connected to one side of the shaft, and the second wire may have one end which is connected to the other side of the moving member, and the other end which is connected to the other side of the shaft, and the second wire may have a middle portion which is wound on the changing pulley so that a moving direction of the second wire is changed.

In accordance with another aspect of the present invention, an ultrasonic diagnostic apparatus includes a probe including a transducer installed to be rotatable, a driving device configured to rotate the transducer, a handle case configured to accommodate the driving device therein, a cap coupled to the handle case to accommodate the transducer therein, and filled with oil, and a diaphragm formed of a deformable material so that a volume of the diaphragm is changed, and disposed in the cap.

The diaphragm may be formed in one of a rectangular parallelepiped, a cylinder, a hemisphere and a triangular pyramid that are hollow.

The diaphragm may include at least one crease.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
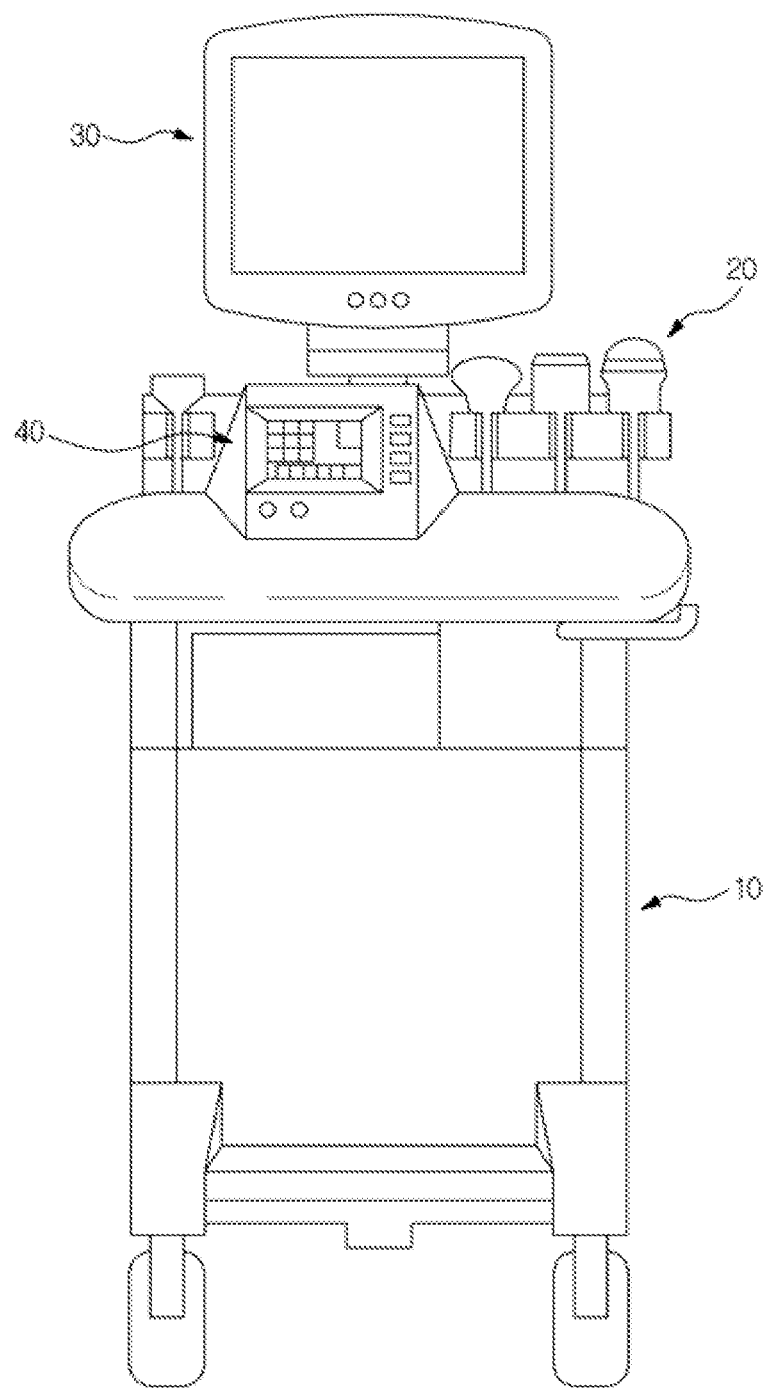
FIG. 1 is a front view of an ultrasonic diagnostic apparatus according to one embodiment of the present invention.

Reference will now be made in detail to the embodiments of the present invention, examples of which are illustrated in the accompanying drawings, wherein like reference numerals refer to like elements throughout.

Hereinafter, an ultrasonic diagnostic apparatus according to an embodiment of the present invention will be described in detail with reference to the drawings.

As illustrated in FIG. 1, an ultrasonic diagnostic apparatus according to an embodiment of the present invention includes a body 10, a probe 20 configured to transmit ultrasonic waves to an object to be diagnosed and receive the ultrasonic waves reflected from the object, a display unit 30 disposed at an upper portion of the body 10 to display a diagnostic result obtained through the received ultrasonic waves using an image, and a control panel 40 configured to allow a user to operate the ultrasonic diagnostic apparatus.

Figure 2:
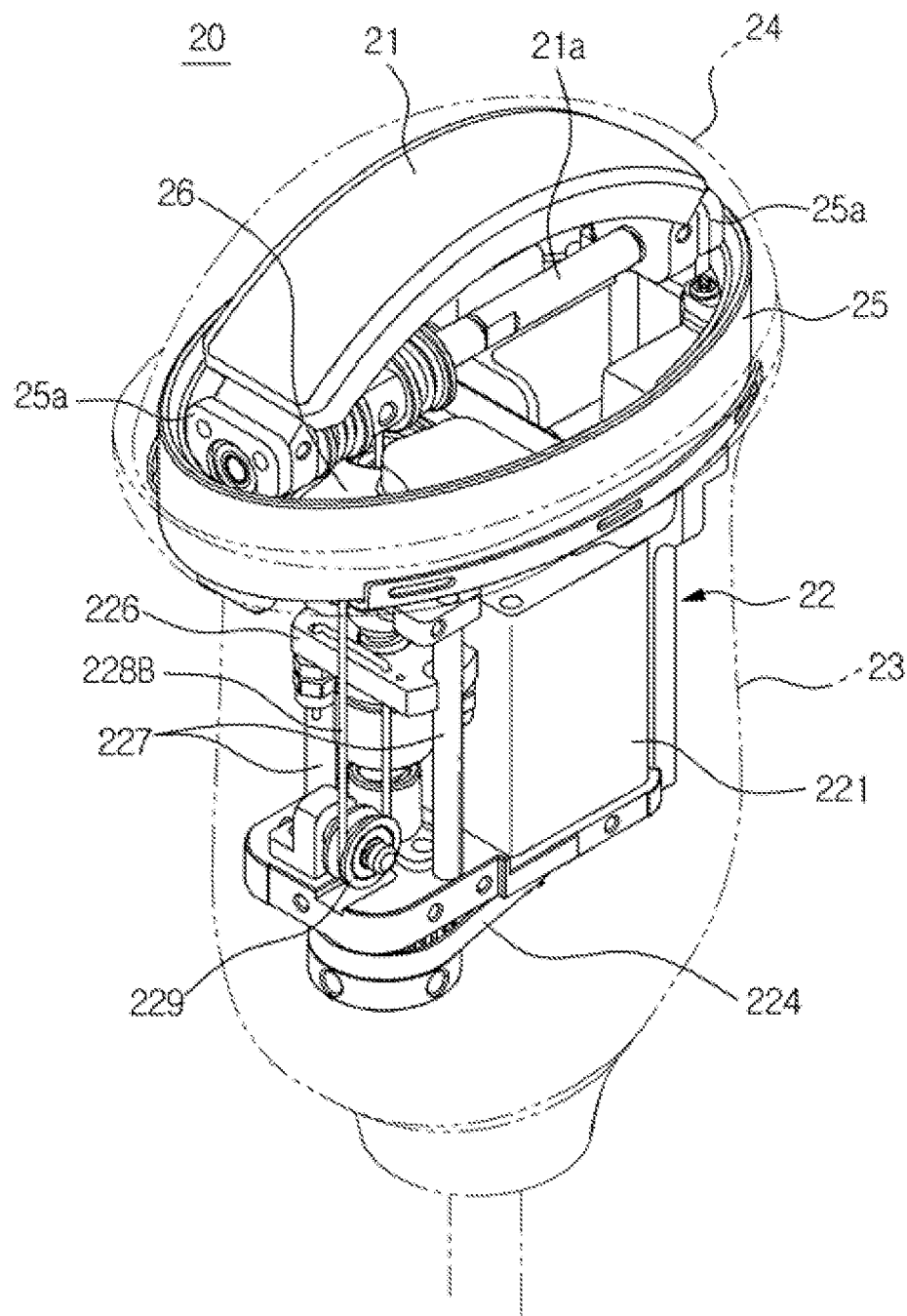
FIG. 2 is a perspective view illustrating an internal configuration of a probe applied to the ultrasonic diagnostic apparatus according to one embodiment of the present invention.
Figure 3:
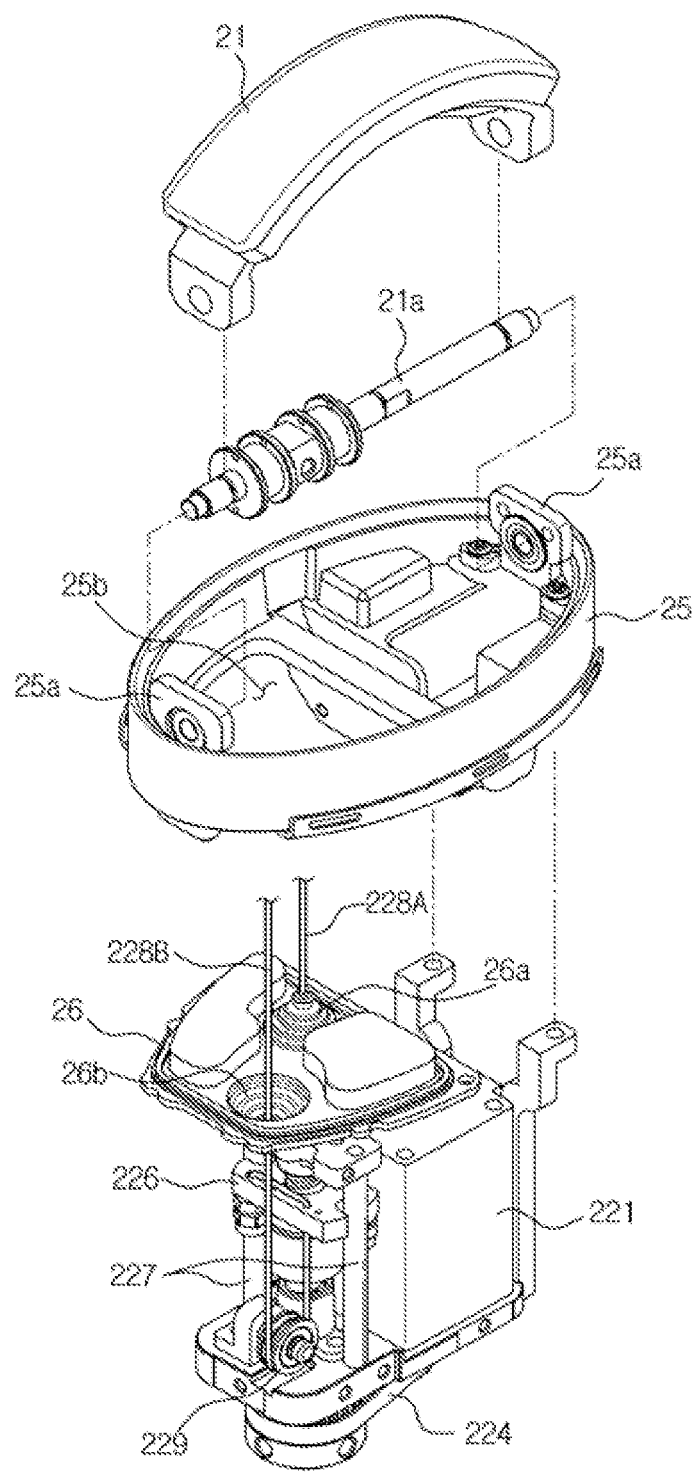
FIG. 3 is an exploded perspective view illustrating the internal configuration of the probe applied to the ultrasonic diagnostic apparatus according to one embodiment of the present invention.

As illustrated in FIGS. 2 and 3, the probe 20 includes a transducer 21 installed to be rotatable, a driving device 22 configured to generate power to rotate the transducer 21, a handle case 23 configured to accommodate the driving device 22 therein and to allow the user to grasp the handle case 23 and use the probe 20, and a cap 24 configured to accommodate the transducer 21 therein and disposed at a distal end of the handle case 23 to be in contact with the object to be diagnosed.

The transducer 21 includes an ultrasonic vibrator configured to transmit and receive the ultrasonic waves and, as described above, may be rotatably installed in the cap 24 to read a three-dimensional image of the object to be diagnosed. The transducer 21 includes a shaft 21a configured to form a rotational center thereof, and both ends of the shaft 21a are rotatably installed at two hinge portions 25a of a partition member 25, which will be described later, to be rotated around the shaft 21a.

A portion of the cap 24 corresponding to the rotating transducer 21 has an arc shape in section so that an interval between an inner surface of the cap 24 and an outer surface of the transducer 21 can be maintained constantly even when the transducer 21 installed in the cap 24 rotates.

An inner space of the cap 24 is filled with oil serving as a medium for transmitting the ultrasonic waves generated from the transducer 21, and the partition member 25 configured to partition the inner space of the cap 24 and an inner space of the handle case 23 is disposed between the cap 24 and the handle case 23, such that the space filled with the oil is defined by the cap 24 and the partition member 25.

As described above, the partition member 25 is installed at the distal end of the handle case 23, and the driving device 22 is fixed in the handle case 23.

Figure 4:
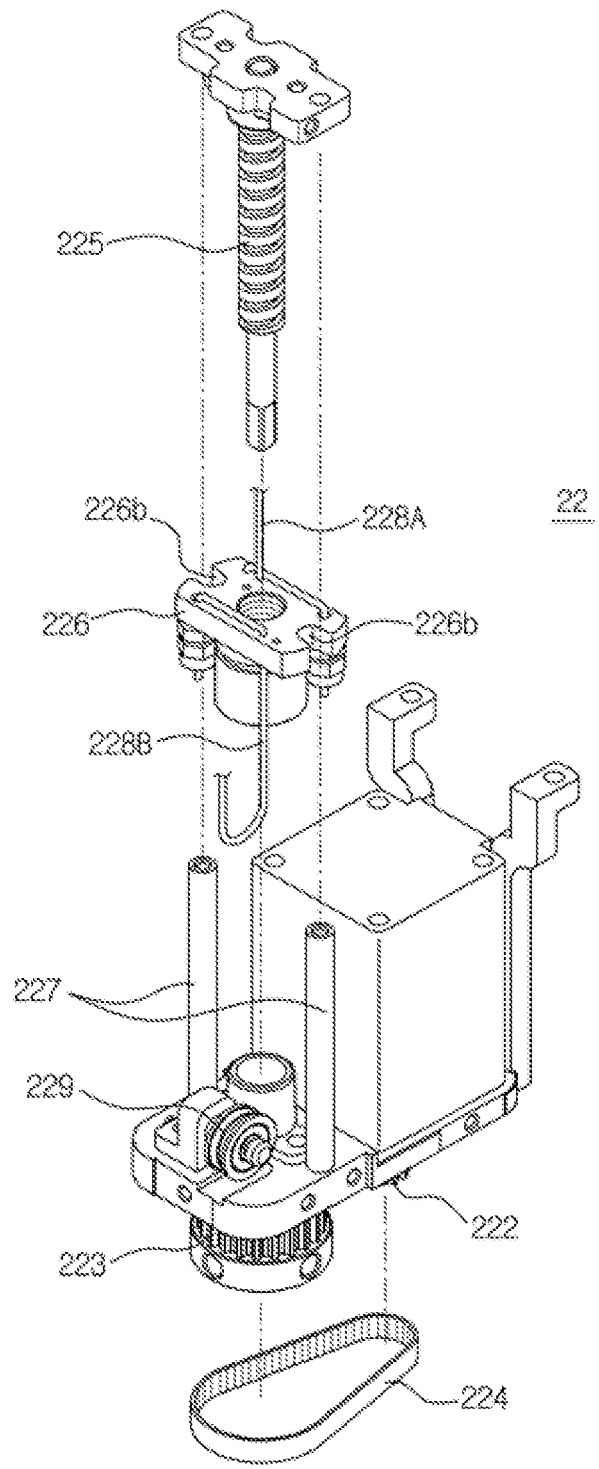
FIG. 4 is an exploded perspective view illustrating a driving device of the probe applied to the ultrasonic diagnostic apparatus according to one embodiment of the present invention.
Figure 5:
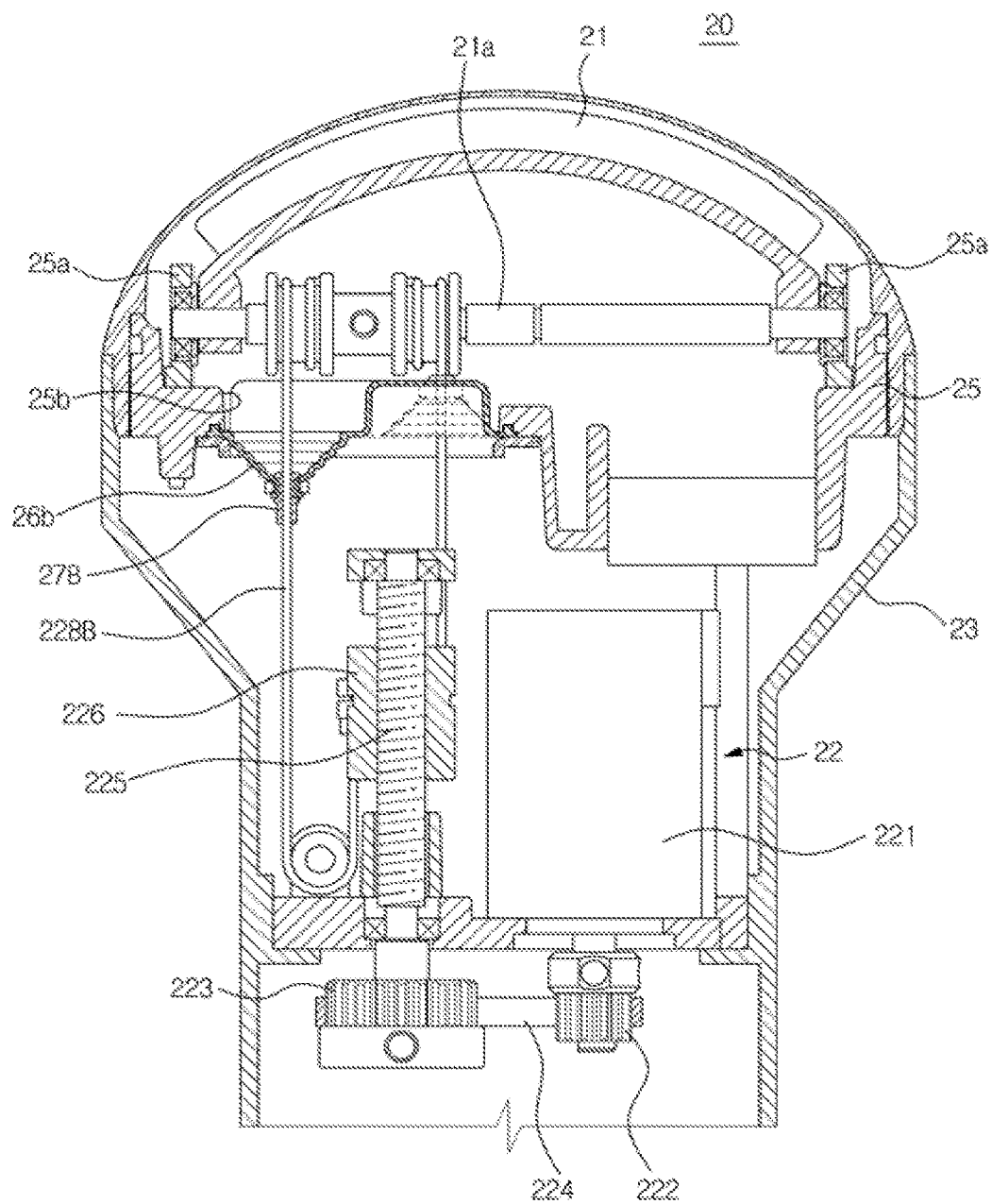
FIG. 5 is a schematic view illustrating an operation of the probe applied to the ultrasonic diagnostic apparatus according to one embodiment of the present invention.
Figure 6:
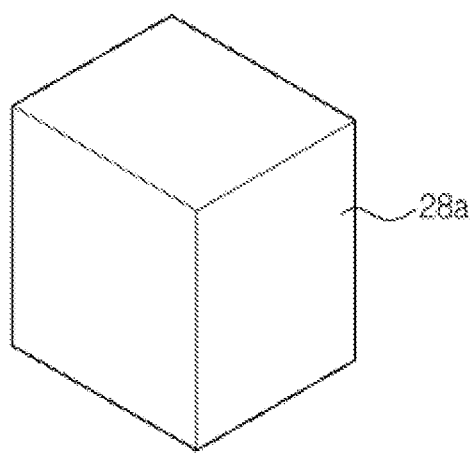
FIGS. 6 to 15 are perspective views respectively illustrating a diaphragm applied to the probe according to another embodiments of the present invention.
Figure 7:
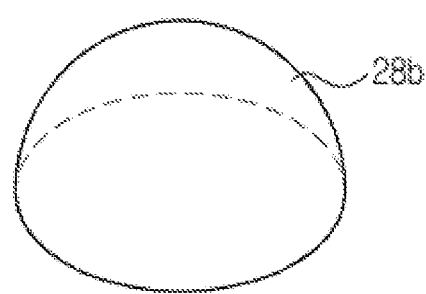
Figure 8:
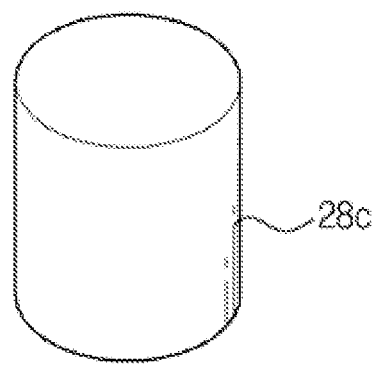
Figure 9:
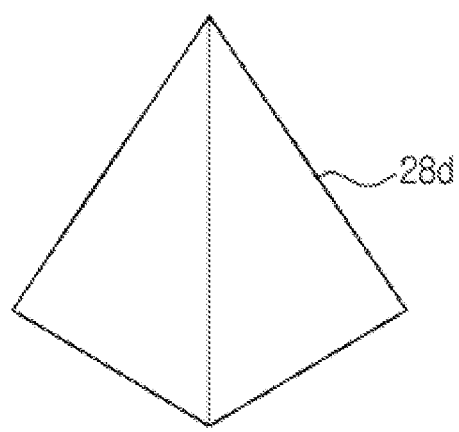
Figure 10:
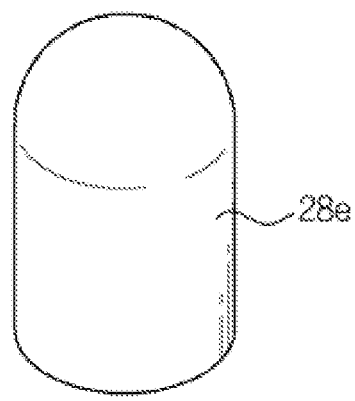
Figure 11:
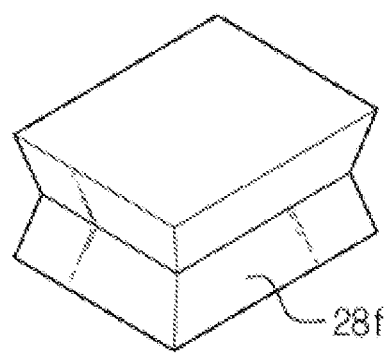
Figure 12:
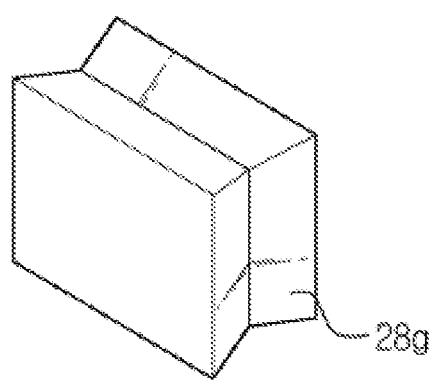
Figure 13:
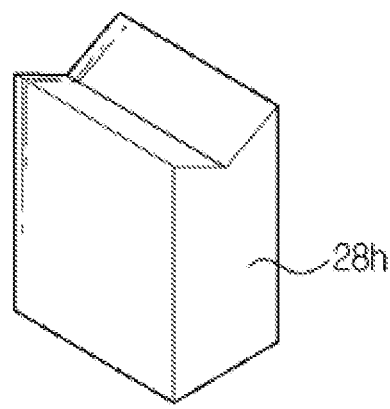
Figure 14:
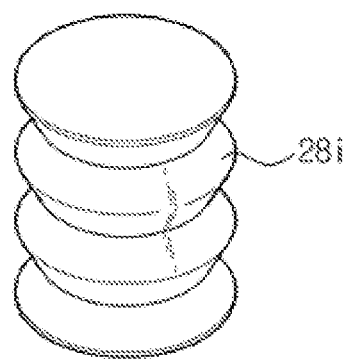
Figure 15:
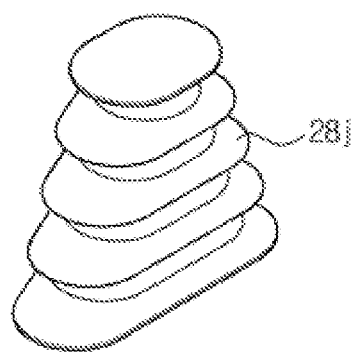

As illustrated in FIGS. 4 and 5, the driving device 22 includes a driving motor 221 configured to generate a rotational force, a driving pulley 222 configured to be rotated by the driving motor 221, a driven pulley 223 configured to receive power from the driving pulley 222 through a timing belt 224, a transfer screw 225 connected to the driven pulley 223 to be rotated together with the driven pulley 223, a moving member 226 configured to be moved according to movement of the transfer screw 225, a pair of guide rods 227 configured to guide movement of the moving member 226, and wires 228A and 228B configured to connect the moving member 226 and the transducer 21 so that the transducer 21 is rotated according to the movement of the moving member 226.

The moving member 226 includes a coupling hole 226a through which the transfer screw 225 passes to be coupled therein, and a pair of guide grooves 226b provided at both sides thereof and installed at the guide rods 227 so that the movement of the moving member 226 is guided by the guide rods 227. Therefore, the moving member 226 is moved in one direction or an opposite direction according to a rotational direction of the transfer screw 225.

The wires 228A are 228B are configured to pass through the partition member 25 and to be connected to the shaft 21a of the transducer 21 to rotate the transducer 21, and the partition member 25 has a through-hole 25b through which the wires 228A and 228B passes through to be installed therein.

The wires 228A and 228B include a first wire 228A of which one end is connected to one side of the moving member 226 and the other end is connected to one side of the shaft 21a so that the shaft 21a is rotated in a first direction, and a second wire 228B of which one end is connected to the other side of the moving member 226 and the other end is connected to the other side of the shaft 21a so that the shaft 21a is rotated in a second direction opposite to the first direction.

Further, the driving device 22 includes a changing pulley 229 which changes a moving direction of the second wire 228B in an opposite direction so that the second wire 228B is moved in a direction opposite to that of the first wire 228A and applies a force to the shaft 21a. Therefore, the second wire 228B has a middle portion which is wound on the changing pulley 229 so that the moving direction thereof is changed reversely.

The partition member 25 includes the pair of hinge portions 25a to which the both ends of the shaft 21a are rotatably installed, and the through-hole 25b through which the wires 228A and 228B pass to be installed therein. A diaphragm 26 which is formed of a deformable material, to which the wires 228A and 228B are fixed, and which is deformed according to movement of the wires 228A and 228B is installed at the through-hole 25b.

The diaphragm 26 is formed of a stretchable material which is elastically deformed like rubber, and includes a first deforming portion 26a through which the first wire 228A passes to be fixedly installed therein and which is deformed according to movement of the first wire 228A, and a second deforming portion 26b through which the second wire 228B passes to be fixedly installed therein and which is deformed according to movement of the second wire 228B. In the embodiment, each of the first and second deforming portions 26a and 26b has a bellows shape to be easily deformed.

Further, sealing members 27A and 27B are installed between the wires 228A and 228B and the deforming portions 26a and 26b to seal between the wires 228A and 228B and the deforming portions 26a and 26b. The sealing members 27A and 28B include a first sealing member 27A through which the first wire 228A passes through to be fixedly installed therein and which is installed to pass through the first deforming portion 26a and to seal between the first wire 228A and the first deforming portion 26a, and a second sealing member 27B through which the second wire 228B passes through to be fixedly installed therein and which is installed to pass through the second deforming portion 26b and to seal between the second wire 228B and the second deforming portion 26b.

Therefore, the first wire 228A and the second wire 228B are moved in opposite directions to each other according to the movement of the moving member 226, and the first deforming portion 26a and the second deforming portion 26b are deformed to correspond to the movements of the first and second wires 228A and 228B, and thus the oil filled in the cap 24 is prevent from leaking.

In the embodiment, the diaphragm 26 is configured so that the deforming portions 26a and 26b are fixed to the wires 228A and 228B and deformed according to the movement of the wires 228A and 228B. However, the present invention is not limited thereto, and the diaphragm may be separately installed from the wires and may correspond to a change of an oil volume in the cap 24 according to a temperature thereof.

That is, as described above, the diaphragm is formed of the deformable material to be deformable, and thus a volume of the diaphragm may be changed. Therefore, in the case in which the temperature of the oil in the cap 24 becomes lower than a reference temperature and the oil volume is reduced, the diaphragm is deformed so that the volume thereof is increased to correspond to the reduced oil volume. In the case in which the temperature of the oil in the cap 24 becomes higher than the reference temperature and the oil volume is increased, the diaphragm is deformed so that the volume thereof is reduced to correspond to the increased oil volume. Therefore, an oil pressure in the cap 24 may be maintained constantly.

Various shapes of the diaphragm performing such operations are illustrated in FIGS. 6 to 15.

As illustrated in FIGS. 6 to 10, the diaphragms 28a to 28e may have various shapes, such as a rectangular parallelepiped, a cylinder, a hemisphere, a triangular pyramid and another deformed shape thereof that are hollow. And as illustrated in FIGS. 11 to 15, the diaphragms 28f to 28j may have one or more creases to be more easily deformable.

As described above, since the diaphragm is deformed according to the movement of the wire configured to rotate the transducer, and corresponds to the movement of the wire, the oil in the cap can be prevented from leaking to the handle case.

Further, as described above, since the diaphragm is deformed to correspond to the change of the oil volume in the cap according to a temperature thereof, the oil pressure in the cap can be maintained constantly.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A probe comprising:
   a transducer installed to be rotatable;
   a driving device configured to rotate the transducer;
   at least one wire configured to transmit power of the driving device to the transducer;
   a handle case configured to accommodate the driving device therein;
   a cap coupled to the handle case to accommodate the transducer therein, and filled with oil; and
   a diaphragm formed of a deformable material and disposed between the cap and the handle case,
   wherein the wire is installed to pass through the diaphragm, and fixed to the diaphragm so that the diaphragm is deformed according to movement of the wire.

2. The probe according to claim 1, wherein the diaphragm is formed of a stretchable material which is elastically deformed.

3. The probe according to claim 2, wherein the driving device comprises a driving motor configured to generate a rotational force, a transfer screw configured to be rotated by the driving motor, and a moving member configured to be moved in an axial direction of the transfer screw according to rotation of the transfer screw, and
   the first wire and the second wire are connected to the moving member so that the first wire and the second wire are moved according to movement of the moving member.

4. The probe according to claim 1, further comprising a partition member disposed between the cap and the handle case to partition an internal space of the cap and an internal space of the handle case,
   wherein the partition member comprises a through-hole in which the diaphragm is installed.

5. The probe according to claim 1, further comprising a shaft connected to a rotational center of the transducer,
   Wherein the wire comprises a first wire connected to one side of the shaft so that the shaft is rotated in a first direction, and a second wire connected to the other side of the shaft so that the shaft is rotated in a second direction.

6. The probe according to claim 5, wherein the diaphragm comprises a first deforming portion through which the first wire passes to be fixedly installed therein and which is deformed according to movement of the first wire, and a second deforming portion through which the second wire passes to be fixedly installed therein and which is deformed according to movement of the second wire.

7. The probe according to claim 6, further comprising:
   a first sealing member through which the first wire passes to be fixedly installed therein, installed to pass through the first deforming portion, and configured to seal between the first deforming portion and the first wire; and
   a second sealing member through which the second wire passes to be fixedly installed therein, installed to pass through the second deforming portion, and configured to seal between the second deforming portion and the second wire.

8. The probe according to claim 6, wherein each of the first deforming portion and the second deforming portion has a bellows shape.

9. The probe according to claim 8, wherein the driving device comprises a changing pulley configured to change an extending direction of the second wire,
   the first wire has one end which is connected to one side of the moving member, and the other end which is connected to one side of the shaft,
   the second wire has one end which is connected to the other side of the moving member, and the other end which is connected to the other side of the shaft, and the second wire has a middle portion which is wound on the changing pulley so that a moving direction of the second wire is changed.

10. An ultrasonic diagnostic apparatus comprising the probe according to claim 1.

11. A probe comprising:
a transducer installed to be rotatable;
a driving device configured to rotate the transducer;
a handle case configured to accommodate the driving device therein;
a cap coupled to the handle case to accommodate the transducer therein, and filled with oil; and
a diaphragm formed of a deformable material to correspond to a volume change of the oil in the cap, and disposed in the cap,
wherein the diaphragm comprises a first deforming portion to which a first portion of the driving device is coupled and which is deformed according to movement of the first portion of the driving device, and a second deforming portion to which a second portion of the driving device is coupled and which is deformed according to movement of the second portion of the driving device.

12. The probe according to claim 11, wherein the diaphragm is formed in one of a rectangular parallelepiped, a cylinder, a hemisphere and a triangular pyramid that are hollow.

13. The probe according to claim 12, wherein the diaphragm comprises at least one crease.

* * * * *